US00PP11353P

United States Patent [19]

Weerdenburg et al.

[11] Patent Number: Plant 11,353

[45] Date of Patent: Apr. 18, 2000

[54] FLORIBUNDA ROSE PLANT NAMED 'KORMEERAM'

[75] Inventors: Andreas J. Weerdenburg, Amstelveen; Hette Spek, Boskoop, both of Netherlands

[73] Assignee: Bear Creek Gardens, Inc., Medford, Oreg.

[21] Appl. No.: 09/138,831

[22] Filed: Aug. 24, 1998

[51] Int. Cl.[7] ..... A01H 5/00

[52] U.S. Cl. ..... Plt./149

[58] Field of Search ..... Plt./141, 149, 130, Plt./138

*Primary Examiner*—Howard J. Locker

*Attorney, Agent, or Firm*—Klarquist Sparkman Campbell Leigh & Whinston, LLP

[57] ABSTRACT

Floribunda rose plant having a dark pink flower color; high flower production; excellent vase life; good shipping qualities; and very vigorous growth habit.

1 Drawing Sheet

The present invention relates to a new and distinct variety of rose plant of the floribunda class which was discovered as a single branch spontaneous flower color mutation on a rose plant of the variety of 'KORmiller' (U.S. Plant Pat. application No. 08/985,371, filed Dec. 4, 1997) growing in a greenhouse in Amstelveen, Holland, which bore a dark pink flower as compared to the pastel pink flowers of 'KORmiller'.

'KORmeeram' differs from its parent, 'KORmiller', principally in flower color and in the color spot at the base of the petals. It has the same growth, production good shippping qualities of cut flowers, vase life and response to the environment as 'KORmiller', producing 26–29 flowers per plant per year in a greenhouse.

Asexual reproduction of this new variety by budding, as performed at Boskoop, Holland, and Somis, Calif. shows that the foregoing and all other characteristics and distinctions come true to form and are established and transmitted through succeeding propagations.

The accompanying illustration shows a typical specimens of the vegetative growth and flowers of this new vareity in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage: Spontaneous mutant of 'KORmiller' (U.S. Plant Pat. application No. 08/985,371, filed Dec. 4, 1997.)

Classification:

*Botanical.*—Rosa hybrida.

*Commercial.*—Floribunda.

FLOWER

Observations made from specimens grown in a greenhouse environment at Boskoop, Holland, and Somis, Calif. from January 1997 to June 1998.

Blooming habit: Continuous.

Bud:

*Size.*—About 1½ inches long when the petals start to unfurl.

*Form.*—Long, pointed ovoid and somewhat blunt at the tip.

*Color.*—When sepals first divide, bud color is Red-Purple Group 57D. When half blown, the upper sides of the petals are Red-Purple Group 57C, and the lower sides of the petals are Red-Purple Group 57D.

*Sepals.*—Color: Green Group 138B. Surface texture: Covered in fine hairs. There are three normally to heavily appendaged sepals. There are two unappendaged sepals with hairy edges.

*Receptacles.*—Color: Yellow-Green Group 146C. Shape: Funnel. Size: Medium (about 5/16 inch×¼ inch). Surface: Smooth.

*Peduncle.*—Length: Short, averaging about 2½ inches. Surface: Smooth. Color: Yellow-Green Group 146C. Strength: Stiff, erect.

Bloom:

*Size.*—Medium. Average open diameter is about 3½ to 4 inches.

*Borne.*—Singly and occasionally on new basal shoots several together in pyramidal clusters of five to seven blooms.

*Stems.*—Strong, averaging about 18–22 inches in length.

*Form.*—When first open: High centered. Permanence: Retains its form to the end, outer petals curl back, quill fashion.

*Petalage.*—Number of petals under normal conditions: 25 to 30.

*Color.*—The upper sides of the petals are Red-Purple Group 57C. The reverse sides of the petals are Red-Purple Group 57D. The base of the petals has a quite large, ⅜"×7/16" Yellow Group 7C half-moon at the point of attachment. The major color on the upper sides is Red-Purple Group 57C.

*Variegations.*—Occasional greenish-white streak on the guard petals.

*Discoloration.*—At the end of the first day: No change. At the end of the third day: No change. By day six on the plant and by day ten in the vase, there is a slight fading of the bloom to Red-Purple Group 66B.

*Fragrance.*—Slight.

Petals:

*Texture.*—Thick, leathery.

*Shape.*—Round.

*Form.*—Tips slightly recurved, edges slightly quilled.

*Arrangement.*—Imbricated. Petaloids in the center are few, small.

*Persistence.*—Petals drop off cleanly before drying.

*Lastingness.*—On the plant: Long (about 9 to 10 days). As a cut flower: Very long (16 to 18 days).

Reproductive parts:

*Anthers.*—Size: Medium. Quantity: Many. Color: Yellow-Orange Group 15A. Arrangement: Regular around styles.

*Filaments.*—Color: Yellow Group 13A.

*Pollen.*—Color: Gold-yellow.

*Styles.*—Color: Greyed-Purple Group 187D.

*Stigmas.*—Color: Greenish-white.

Plant:

*Form.*—Bush.

*Growth.*—Very vigorous; upright; branching. Mature plant, six to seven months after planting, is 5½ feet in height and 3½ feet in width. Plants are maintained at this height and width by harvest of flowers.

Foliage: Number of leaflets on normal mid-stem leaves: Five.

*Size.*—Large (6½ inches long×4¾ inches wide).

*Quantity.*—Abundant.

*Color.*—New foliage: Upper side and lower sides: Greyed-Purple Group 184B. Old foliage: Upper side: Green Group 139A. Lower side: Green Group 137C. The foliage upper surface will rapidly turn green, while the lower surface will keep the Greyed-Purple Group 184B for several days before becoming green.

Leaflets:

*Shape.*—Pointed oval.

*Texture.*—Leathery. Surface: Matte.

*Edge.*—Serrated.

*Serration.*—Single, small.

*Petiole Rachis.*—Color: Greyed-Purple Group 187B.

*Petiole Underside.*—Smooth.

*Stipules.*—Medium (⅝), serrated, bearded.

*Disease Resistance.*—Resistant to mildew under normal growing conditions in a greenhouse. Not tested for resistance to blackspot and rust.

Wood:

*New Wood.*—Color: Greyed-Purple Group 187B. Bark: Smooth.

*Old Wood.*—Color: Green Group 139A. Bark: Smooth.

Prickles:

*Quantity.*—On main canes from base: Few. On laterals from main canes: Few.

*Form.*—Short, hooked slightly downward.

*Color when Young.*—Greyed-Purple Group 187B.

*Color when Mature.*—Near Greyed-Orange Group 174D.

Small prickles:

*Quantity.*—On main stalks: None. On laterals: None.

I claim:

1. A new and distinct variety of rose plant of the floribunda class, as herein shown and described, characterized particularly by its dark pink flower color; high flower production; excellent vase life; good shipping qualities; and very vigorous growth habit.

* * * * *

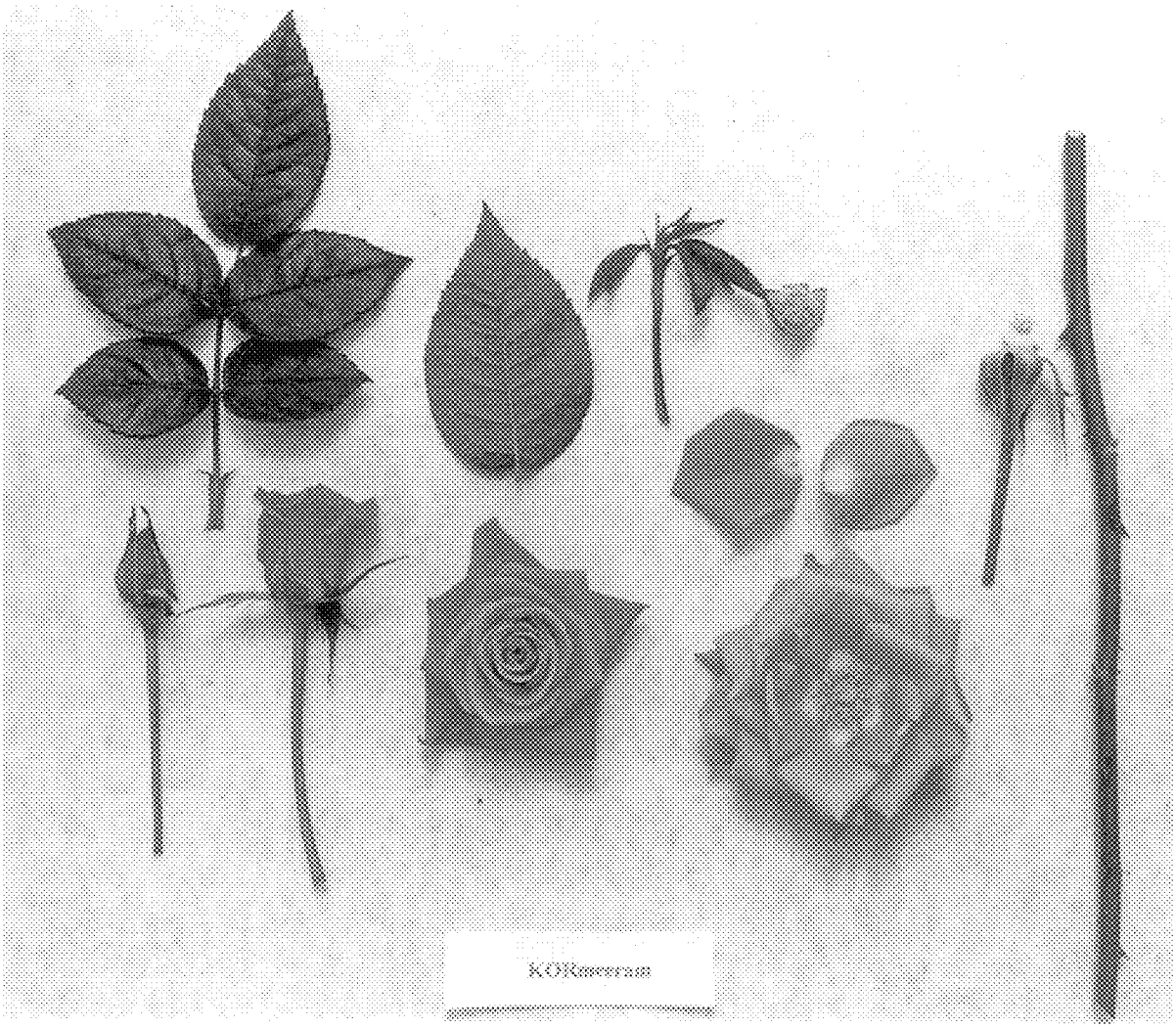
KORsperan